United States Patent [19]

Borchers

[11] 4,159,716

[45] Jul. 3, 1979

[54] METHOD OF COMPRESSING AND REALIGNING BONE STRUCTURES TO CORRECT SPLAY FOOT

[76] Inventor: Clinton H. Borchers, 740 Reading Rd., Mason, Ohio 45040

[21] Appl. No.: 842,625

[22] Filed: Oct. 17, 1977

[51] Int. Cl.$^2$ .......................... A61F 5/00; A61B 17/18
[52] U.S. Cl. ............................... 128/80 R; 128/92 A; 128/92 B; 128/92 EA; 128/92 EB
[58] Field of Search .................. 128/69, 77, 80 R, 83, 128/84 R, 84 B, 92 R, 92 A, 92 E, 92 EA, 92 EB

[56] References Cited

U.S. PATENT DOCUMENTS

| | | | |
|---|---|---|---|
| 2,346,346 | 4/1944 | Anderson | 128/92 A |
| 2,434,431 | 1/1948 | Pincock | 128/92 A |

FOREIGN PATENT DOCUMENTS

| | | | |
|---|---|---|---|
| 210985 | 9/1960 | Austria | 128/83 |
| 157757 | 1/1964 | U.S.S.R. | 128/84 R |

OTHER PUBLICATIONS

"A Drilling Jig for Arthrodesis of the Hip", by C. A. Cass et al., The Journal of Bone & Joint Surgery, British vol. 51-B, No. 1, Feb. 1969, pp. 135–139.

Kirschner Wires, Threaded Kirschner Wires, Orthopedic Catalog, Richards Mfg. Co., Memphis, Tenn., received in PTO Scientific Library on Mar. 25, 1975, p. 118.

Primary Examiner—Ronald L. Frinks
Attorney, Agent, or Firm—Melville, Strasser, Foster & Hoffman

[57] ABSTRACT

Apparatus and method for compression and realignment of animal bone structures and passage of a drill pin therethrough to retain them in a desired alignment. The apparatus comprises a rigid U-shaped jig having a threaded aperture adjacent the end of one leg and an unthreaded aperture adjacent the end of the other leg thereof, the apertures being axially aligned; a threaded adjustment screw engaged in the threaded aperture and movable toward the other leg upon rotation; a cylindrical bushing slidably engaged in the unthreaded aperture having a threaded axial passage therethrough; means for clamping the bushing in a desired position of adjustment; a threaded drill pin engaged in the passage in the bushing and movable toward the one leg upon rotation; and means for rotating the drill pin thereby piercing and traversing the bone structures and holding them in a desired position of alignment. Correction of splay foot deformity and other surgery of the human foot, hand and knee can thus be effected.

1 Claim, 4 Drawing Figures

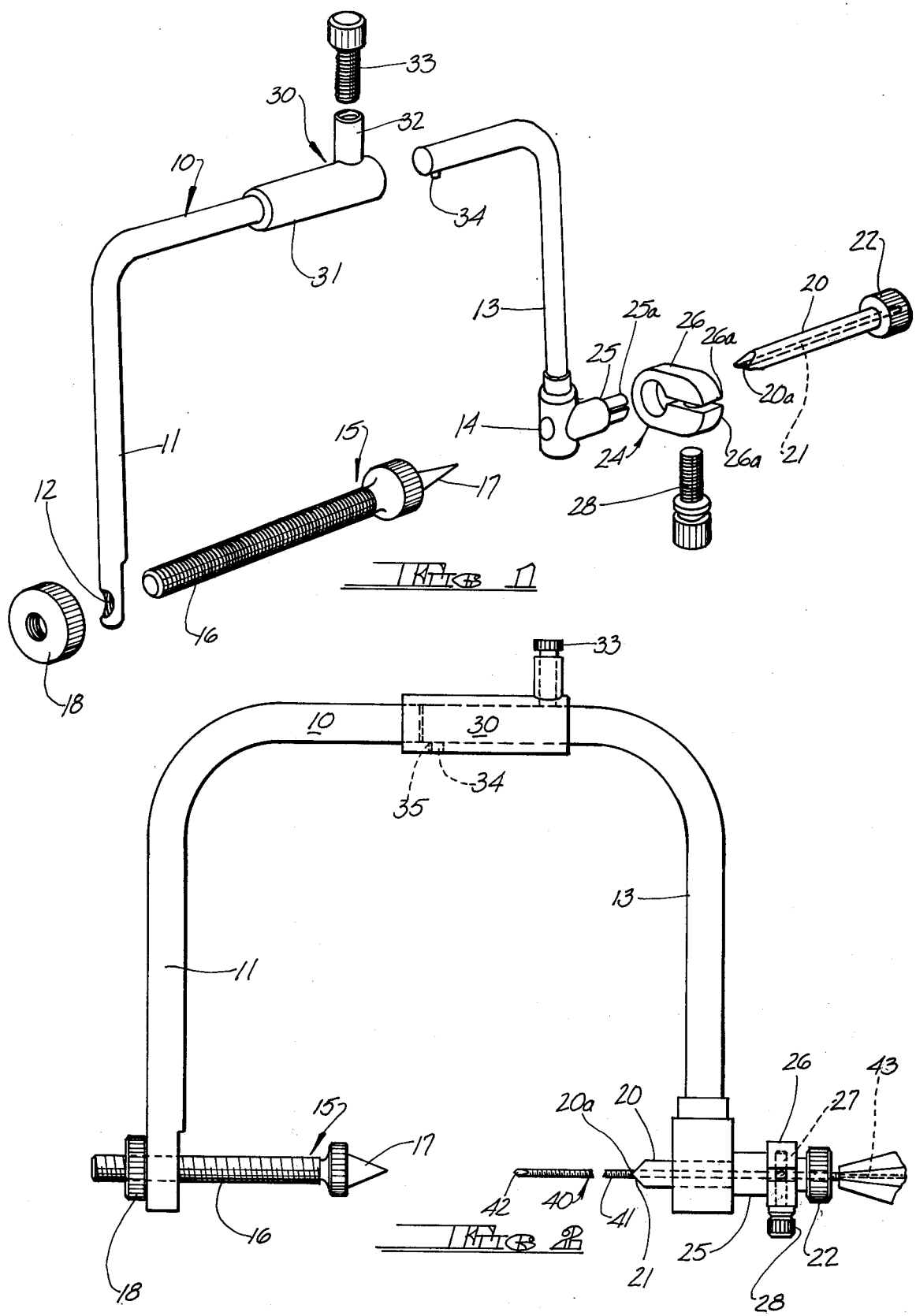

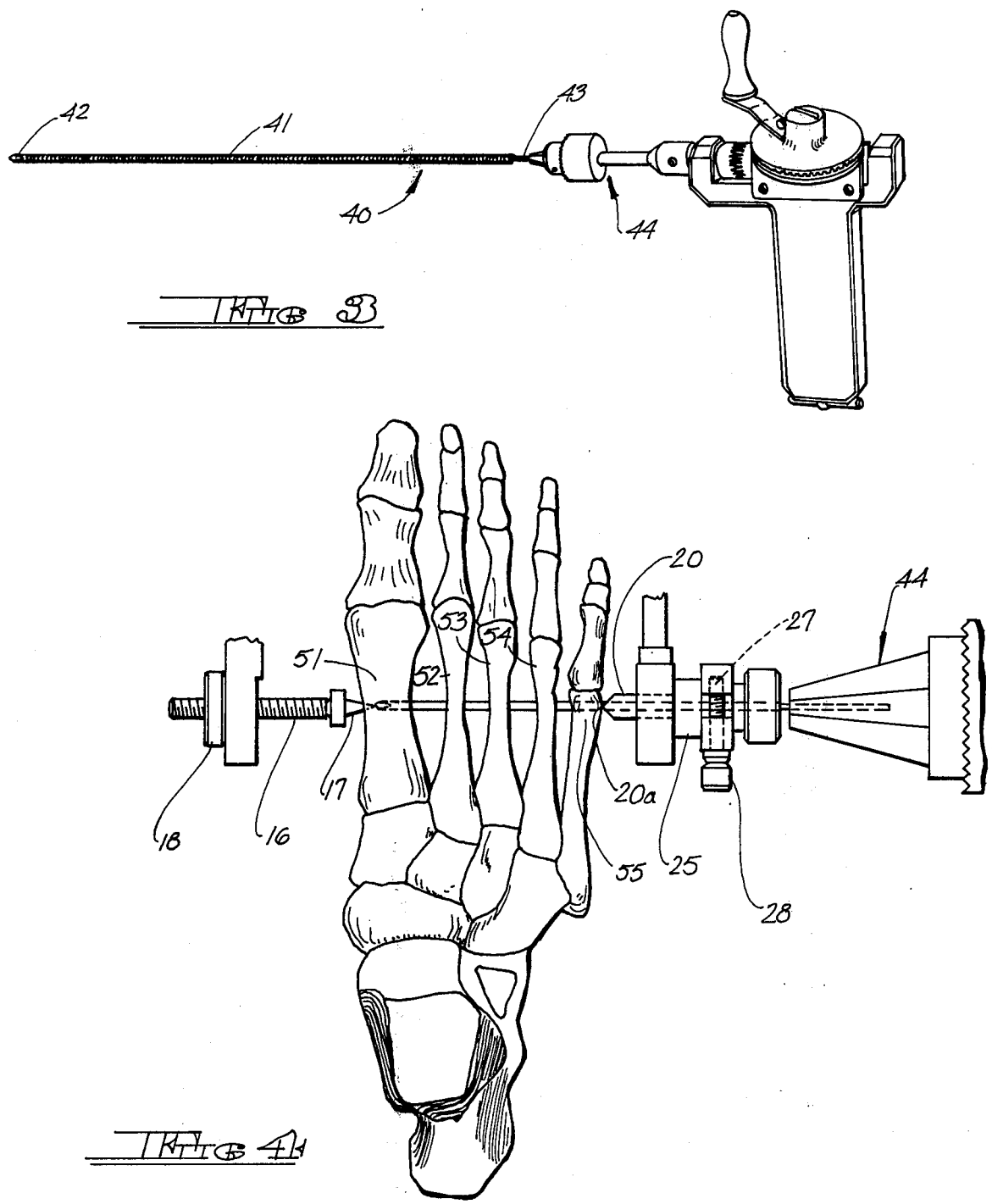

METHOD OF COMPRESSING AND REALIGNING BONE STRUCTURES TO CORRECT SPLAY FOOT

BACKGROUND OF THE INVENTION

This invention relates to apparatus and method for the compression and realignment of animal bone structures and passage of a drill pin through bone structures to retain them in a desired alignment, particularly in surgery of the human foot, hand and knee. Although not so limited, the apparatus and method of the invention have particular utility in the correction of splay foot deformity wherein the forepart of the foot is wider than normal.

In the surgical correction of splay foot deformity it is necessary to compress the forepart of the foot, thus realigning the metatarsal shafts, and then to drive a threaded drill pin through the fifth metatarsal head into the first metatarsal shaft or neck. Such an operation requires precise compression and realignment of the metatarsal shafts and precise insertion of the drill pin.

United States Pat. No. 3,441,017 discloses a jig for drilling through a tubular bone. U.S. Pat. No. 3,867,932 discloses a jig and drill assembly for inserting rigid shafts into fractured bones.

SUMMARY

It is a principal object of the present invention to provide apparatus and method which will effect precise compression, realignment and passage of a drill pin through bone structures in surgery of the foot and hand.

According to the invention, apparatus for the compression and realignment of animal bone structures and passage of the drill pin therethrough to retain the bone structures in a desired alignment comprises a generally U-shaped jig, the jig having a threaded aperture adjacent the end of one leg thereof and an unthreaded aperture adjacent the end of the other leg thereof, these apertures being axially aligned; a threaded adjustment screw adapted to engage in the threaded aperture and to move toward the other leg when rotated; a cylindrical bushing adapted for slidable engagement in the unthreaded aperture and having a threaded axial passage therethrough; means for clamping the bushing in a desired position in the unthreaded aperture; an elongated, threaded drill pin adapted to engage in the passage through the bushing and to move toward the one leg when rotated; and means for rotating the drill pin, whereby rotation of the adjustment screw and the drill pin toward one another compresses and realigns the bone structures, and continued rotation of the drill pin causes it to pierce and traverse the bone structures thereby holding them in a desired alignment.

The method of the present invention comprises the steps of aligning two adjustable members on opposite sides of the bone structures which are to be compressed and realigned, moving the members inwardly toward and in axial alignment with one another, clamping the members in relatively immovable positions, inserting a threaded drill pin through an axial threaded passage in one of said members, advancing the drill pin by rotation thereof through the passage toward the other of said members and in axial alignment therewith, thereby causing the drill pin to pierce and traverse the bone structures, stopping the advance of the drill pin when the end thereof has penetrated the interior of the most remote therefrom of the bone structures, and severing the drill pin at its point of entry into the closest thereto of the bone structures, whereby a portion of the drill pin interconnects the most remote and closest bone structures to hold them in a desired relatively compressed alignment.

The improved, generally U-shaped jig of the present invention is of rigid construction and is provided with means for adjusting the spacing between the legs thereof and for positioning the threaded aperture in one leg in precise axial alignment with the unthreaded aperture in the other leg.

BRIEF DESCRIPTION OF THE DRAWINGS

Reference is made to the accompanying drawings wherein an exemplary embodiment adapted to the correction of splay foot deformity in human beings is illustrated as follows:

FIG. 1 is a fragmentary perspective view of a jig, adjustment screw, cylindrical bushing and clamping means in dis-assembled relation.

FIG. 2 is a vertical section view of the elements of FIG. 1 in assembled relation;

FIG. 3 is a perspective view of an exemplary drill pin and means for rotation thereof;

FIG. 4 is a view of the bones of a human right foot, dorsal surface, illustrating the manner of placement of a drill pin.

DESCRIPTION OF THE PREFERRED EMBODIMENTS

Referring to FIG. 1, a generally U-shaped jig formed of rigid stainless steel rod stock is shown generally at 10, having one leg 11 adjacent the end of which is provided a threaded aperture 12. The other leg 13 is provided with an unthreaded aperture 14. An adjustment screw indicated generally at 15 is provided with a threaded shaft 16 adapted to be threadably engaged in aperture 12 and to be advance or retracted by rotation thereof. At the opposite, or inwardly facing end of adjustment screw 15 a conical tip 17 is provided for a purpose hereinafter described.

A locking nut, indicated at 18, is preferably provided for maintaining the adjustment screw in a desired position.

A cylindrical guide bushing is shown at 20 comprising a hollow shaft adapted for slidable engagement in the unthreaded aperture 14 in leg 13. The bushing 20 is formed with an axial passage therethrough indicated at 21. Preferably a knurled knob 22 is provided on the outer end of the bushing 20.

Clamping means, shown generally at 24 may comprise a cylindrical sleeve 25 secured to the outwardly facing surface of the end of the leg 13 in alignment with the unthreaded aperture 14 and constituting an extension thereof.

The sleeve 25 is provided with a bifurcated portion 25a, over which an apertured clamp element indicated at 26 may be slidably engaged. The clamp element 26 is further provided with a threaded aperture 27 (FIG. 2) into which a threaded clamp lock bolt 28 is engaged. Upon rotation of the bolt 28 jaws 26a of the clamp element are forced together, thereby constricting the aperture in the clamp element and compressing the bifurcated portion 25a of cylindrical tube 25. When the bushing 20 is inserted through tube 25 and aperture 14, tightening of the clamp lock nut 28 holds the bushing in a desired position of adjustment. It will be understood that equivalent clamp means may be substituted for the elements 25, 26, 27 and 28 described above.

In a preferred embodiment, as shown in FIGS. 1 and 2, the U-shaped jig 10 is comprised of two L-shaped sections joined by adjusting means indicated generally at 30. This means comprises a cylindrical tube 31 one end of which is secured as by welding to one end of one of the L-shaped sections. Perpendicular to the sleeve 31 there is secured an internally threaded sleeve 32 opening into the free end of the sleeve 31 in which a threaded lock bolt or set screw 33 is engaged. Adjacent the end of the other L-shaped section there is provided a detent 34 which engages a slot (not shown) in the sleeve 31.

The arrangement of the adjustment means 30 is such that the slot is caused to engage the detent 34 provided on the other L-shaped section, when the base of the other L-shaped section is slidably inserted in the free end of the sleeve 31 by a distance sufficient to provide the desired spacing between the legs 11 and 13. The lock bolt 33 is then tightened in sleeve 32 to bear against the base of the other L-shaped section, thereby providing a rigid U-shaped structure. It will be apparent that adjustment means 30 thus provides not only for variation in spacing between the legs 11 and 13 but that the detent 34 and mating slot also insure the desired precise axial alignment between the apertures 12 and 14.

The assembled jig, adjustment screw, bushing, clamp means and adjustment means are illustrated in FIG. 2.

Turning next to FIG. 3, a drill pin which is adapted to be inserted through the internally threaded opening 21 of bushing 20 is shown generally at 40. The drill pin may be of conventional type, such as a Kirschner of Steinman pin, and comprises a threaded shaft 41, a flattened and pointed end 42, a reduced diameter section 43 at the opposite end separated by a shoulder from the threaded shaft 41. Crank means 44, such as a Bunnell hand drill, rotate the drill pin. It will be evident that rotation of the drill pin 40 in one direction will cause it to advance through the passage 21 in bushing 22 and pass with slight clearance through tube spacer 25 and unthreaded aperture 14 toward adjustment screw 15 which is engaged in threaded aperture 12.

Reference may next be made to FIG. 4 which shows the bones of a right human foot (dorsal surface) and portions of the apparatus of the present invention, including the drill pin 40 after the latter has been inserted into the desired position.

The first metatarsal neck or shaft is indicated at 51 in FIG. 4, and the second, third and fourth metatarsal shafts are indicated at 52, 53 and 54, respectively. The fifth metatarsal head is shown at 55.

The method of use is as follows:

The assembled apparatus, as shown in FIG. 2, is aligned with the point 17 of adjustment screw 15 on the medial side of the first metatarsal neck 51. Adjustment screw 15 is then rotated to cause the point 17 of adjustment screw 15 to penetrate the medial side of the first metatarsal neck 51. On the lateral side, the clamp means 24 is loosened, and the guide bushing 20, which is provided with an angular point 20a is compressed against the fifth metatarsal head 55 so as to penetrate the lateral side thereof. When correcting splay foot deformity, the bushing 20 is moved toward adjustment screw 15 far enough to compress the bone structures and realign the metatarsal shafts. The clamp means 24 is then tightened to hold bushing 20 in the selected position. The drill pin, which will be 3/32 inch in diameter for correction of splay foot deformity, is then inserted into threaded passage 21 and rotated by means 44, causing it to pierce and penetrate through the head of the fifth metatarsal 55. Continued rotation then causes the drill pin to advance, and with the desired realighment of the metatarsal shafts, the drill pin passes under the fourth, third and second metatarsal shafts successively indicated at 54, 53 and 52, respectively in FIG. 4, and enters the neck or shaft of the first metatarsal 51. The point 42 of pin 40 is caused to penetrate the first metatarsal neck or shaft 51 until it is adjacent the point 17 of adjustment screw 15.

After the pin 40 has been inserted into the desired position in the foot as described above, the adjustment means 30 is lowered, thereby permitting disassembly of the jig, and the drill pin 40 is left inside the foot in the proper position. The portion of the threaded shaft 41 of the pin projecting outwardly on the lateral side of the fifth metatarsal head 55 is cut off with a portion thereof extending out of the foot for purposes of removal, it being understood that the portion of the threaded shaft 41 remaining in the foot maintains the metatarsal shafts of the forepart of the foot in proper alignment.

Post-operative procedure may involve leaving the pin in the foot until the deformity is corrected, generally at least about six weeks, after which it is removed.

Although preferred embodiments of the apparatus and method of the invention have been described above as applied to the correction of splay foot deformity, it will be apparent that the apparatus has broader utility in surgery of the foot, hand and knee where compression and realignment of bony structures and the passage of a pine therethrough is desired for corrective purposes.

Modifications may be made without departure from the spirit and scope of the invention. Thus, the adjustment means 30 may be considered optional, or the obvious mechanical equivalent of the elements thereof described above may be substituted. Similarly, the apparatus of the invention is not restricted to the specific clamp means 24 described above. Accordingly, no limitations are to be inferred except as set forth in the appended claims.

The embodiments of the invention in which an exclusive property or privilege is claimed are defined as follows:

1. A method of compressing and realigning animal bone structures and passing a drill pin therethrough to retain said structures in a desired alignment, as applied to the correction of splay foot deformity in the human foot, comprising the steps of aligning two adjustable members on opposite sides of said bone structures of said human foot, one of said members being aligned on the medial side of the first metatarsal shank and the other of said members being aligned on the lateral side of the fifth metatarsal head, moving said members inwardly toward and in axial alignment with one another, thereby compressing and realigning said bone structures, clamping said members in relatively immovable positions, inserting a threaded drill pin through an axial passage in one of said members, advancing said drill pin by rotation thereof through said passage toward the other of said members and in axial alignment therewith through said fifth metatarsal head, under the fourth, third and second metatarsal shafts successively, and into said first metatarsal shank, thereby causing said drill pin to pierce and traverse said bone structures, stopping the advance of said drill pin when the end thereof has penetrated the interior of the most remote therefrom of the bone structures, and severing said drill pin at its point of entry into said fifth metatarsal head, the closest thereto of the bone structures, whereby a portion of said drill pin interconnects said most remote and closest bone structures to hold them in a desired relatively compressed alignment.

* * * * *